(12) United States Patent
Tachikawa et al.

(10) Patent No.: US 8,675,624 B2
(45) Date of Patent: Mar. 18, 2014

(54) RADIATION IMAGING SYSTEM, METHOD FOR RADIATION IMAGING SYSTEM, AND COMPUTER-READABLE STORAGE MEDIUM

(75) Inventors: Hirohide Tachikawa, Amstelveen (NL); Tadahiko Iijima, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 541 days.

(21) Appl. No.: 12/939,419

(22) Filed: Nov. 4, 2010

(65) Prior Publication Data

US 2011/0116486 A1    May 19, 2011

(30) Foreign Application Priority Data

Nov. 13, 2009  (JP) ................................ 2009-260451
Oct. 27, 2010  (JP) ................................ 2010-241367

(51) Int. Cl.
*H04W 4/00* (2009.01)

(52) U.S. Cl.
USPC ............ 370/338; 370/329; 370/341; 370/350

(58) Field of Classification Search
USPC .......... 370/328, 338, 350; 382/128; 455/41.2, 455/187.1, 525
See application file for complete search history.

(56) References Cited

U.S. PATENT DOCUMENTS

| 7,463,813 | B2 | 12/2008 | Zwart ........................... 385/147 |
| 7,991,292 | B2 | 8/2011 | Takeshita et al. ............. 398/115 |
| 2005/0054369 | A1 | 3/2005 | Murakami ..................... 455/525 |
| 2005/0186906 | A1* | 8/2005 | Hussmann .................... 455/41.2 |
| 2006/0215892 | A1* | 9/2006 | Ohara ............................ 382/128 |
| 2008/0125067 | A1* | 5/2008 | Bells et al. .................. 455/187.1 |
| 2009/0081951 | A1* | 3/2009 | Erdmann et al. ............. 455/41.2 |
| 2009/0286564 | A1* | 11/2009 | Ho ................................ 455/502 |

FOREIGN PATENT DOCUMENTS

| EP | 1857048 | 11/2007 |
| EP | 1959588 | 8/2008 |
| JP | 2006-197063 | 7/2006 |
| JP | 2008-199503 | 8/2008 |
| WO | 2008/111355 A | 9/2008 |

* cited by examiner

*Primary Examiner* — Brian D Nguyen
*Assistant Examiner* — Toan Nguyen
(74) *Attorney, Agent, or Firm* — Fitzpatrick, Cella, Harper & Scinto

(57) ABSTRACT

A radiation imaging system comprises: a radiation imaging apparatus; an entry apparatus which is associated with a radiation generator; wherein the entry apparatus is configured, in response to a request received from the radiation imaging apparatus via a close proximity wireless communication connection, to send information to the radiation imaging apparatus via the close proximity wireless communication connection for connecting the radiation imaging apparatus to a wireless LAN; wherein the close proximity wireless communication connection has a communication range shorter than that of a wireless LAN; and a control unit for controlling the radiation generator and the radiation imaging apparatus, which has connected to the wireless LAN based on the information which has been sent from the entry apparatus via the close proximity wireless communication connection.

14 Claims, 10 Drawing Sheets

FIG. 10A

| APPARATUS \ ID | | | |
|---|---|---|---|
| X-RAY GENERATOR | ID 1 | ID 2 | ID 3 |
| ENTRY APPARATUS | ID 1 | ID 2 | ID 3 |

FIG. 10B

| APPARATUS \ ID | | | |
|---|---|---|---|
| X-RAY GENERATOR | ID 1 | ID 2 | ID 3 |
| X-RAY SENSOR APPARATUS | ID 1 | ID 2 | ID 3 |

# RADIATION IMAGING SYSTEM, METHOD FOR RADIATION IMAGING SYSTEM, AND COMPUTER-READABLE STORAGE MEDIUM

BACKGROUND OF THE INVENTION

1. Field of the Invention

The present invention relates to a radiation imaging system, a method for radiation imaging system, and a computer-readable storage medium that digitize captured radiation images by A/D conversion and send the digitized radiation image data via a wireless communication apparatus.

2. Description of the Related Art

There is available a digital radiation imaging apparatus which digitizes the radiation image captured by the apparatus and generates a sharper radiation image by processing the digitized radiation image. When a plurality of wireless digital X-ray imaging apparatuses are simultaneously operated in a hospital or the like in practice, wireless communication interference between X-ray rooms may hinder the implementation of desired communication performance. Interference between networks based on wireless communication is generally avoided by changing the frequency band used for wireless communication.

As a method to change the radio settings in a radiation sensor apparatus, for example, an X-ray sensor apparatus, a method using a wireless itself is available. For example, according to a wireless LAN standard complying with IEEE802.11, a client (CA) which tries to connect to an access point (AP) has a function of searching for a channel on which the AP exists by performing scanning while dynamically switching its operating frequency bands. Using this function allows to automatically connect to APs set on different channels in the respective X-ray rooms. In this case, however, the CA automatically connects to any AP within the radio range, and hence cannot selectively connect to one of synchronous access points existing in the respective X-ray rooms. Accordingly, it is difficult to perform control in order to synchronize an X-ray sensor apparatus with the desired radiation generator.

On the other hand, the wireless LAN standard covers an encryption function that conceals wireless communication. This function allows a wireless network to be created in each X-ray room by setting an encryption key used for wireless communication between a synchronous access point existing in a given X-ray room and an X-ray sensor apparatus and setting different encryption keys in the respective X-ray rooms. There is an invention configured, in consideration of the above situation, such that an AP and a CA respectively include two types of different wireless communication units to communicate security information such as encryption key information used by the first wireless communication unit via the second wireless communication unit capable of only short range communication (see Japanese Patent Laid-Open No. 2006-197063). A CA can participate in a wireless LAN via an AP which is accessible to the CA.

However, while a CA can participate in a particular wireless LAN in the method disclosed in Japanese Patent Laid-Open No. 2006-197063, in cases wherein there are a plurality of X-ray sensor apparatuses in one or more X-ray rooms or wherein an X-ray apparatus is moved between X-ray rooms, it is difficult to perform control in order to synchronize by wireless communication an X-ray sensor apparatus with the desired radiation generator.

Assume that in an environment in which wireless communication interference occurs, security settings are made by the method disclosed in Japanese Patent Laid-Open No. 2006-197063. In this case, while the X-ray sensor apparatus is linked with a synchronous access point in another X-ray room, the X-ray sensor apparatus may start security setting processing. In such a case, since no encryption key information match is found, the X-ray sensor apparatus discards the existing wireless LAN link and re-connects to a synchronous access point existing on another channel upon scanning. This disadvantageously prolongs the wait time for connection to a network.

As described above, it is difficult to simply and easily create a dedicated wireless LAN network, for each of a plurality of radiation rooms which cause mutual radio interference, between a synchronous access point capable of being connected to a radiation generator and a radiation sensor apparatus existing in a radiation room.

It is also difficult to connect radiation sensor apparatuses to desired wireless networks with a simple and intuitive operation when using the apparatuses while moving and interchanging them between a plurality of radiation rooms.

SUMMARY OF THE INVENTION

In consideration of the above problems, the present invention provides a technique of performing control to synchronize by wireless communication an X-ray sensor apparatus with the desired radiation generator in a case wherein there are a plurality of X-ray sensor apparatuses within an area where wireless waves interfere with each other.

The present invention in its one aspect provides a radiation imaging system comprising: a radiation imaging apparatus; an entry apparatus which is associated with a radiation generator; wherein the entry apparatus is configured, in response to a request received from the radiation imaging apparatus via a close proximity wireless communication connection, to send information to the radiation imaging apparatus via the close proximity wireless communication connection for connecting the radiation imaging apparatus to a wireless LAN; wherein the close proximity wireless communication connection has a communication range shorter than that of a wireless LAN; and a control unit configured to control the radiation generator and the radiation imaging apparatus, which has connected to the wireless LAN based on the information which has been sent from the entry apparatus via the close proximity wireless communication connection.

According to the present invention, it is possible to perform control to synchronize by wireless communication driving of an X-ray sensor apparatus with emission of radiation of the desired radiation generator in a case wherein there are a plurality of X-ray sensor apparatuses within an area where wireless waves interfere with each other.

Further features of the present invention will become apparent from the following description of exemplary embodiments (with reference to the attached drawings).

BRIEF DESCRIPTION OF THE DRAWINGS

FIG. 10A is a view showing an example of how X-ray generators and entry apparatuses are associated with each other; and FIG. 10B is a view showing an example of how X-ray generators and X-ray sensor apparatuses are associated with each other.

DESCRIPTION OF THE EMBODIMENTS

First Embodiment

Figure 1A:
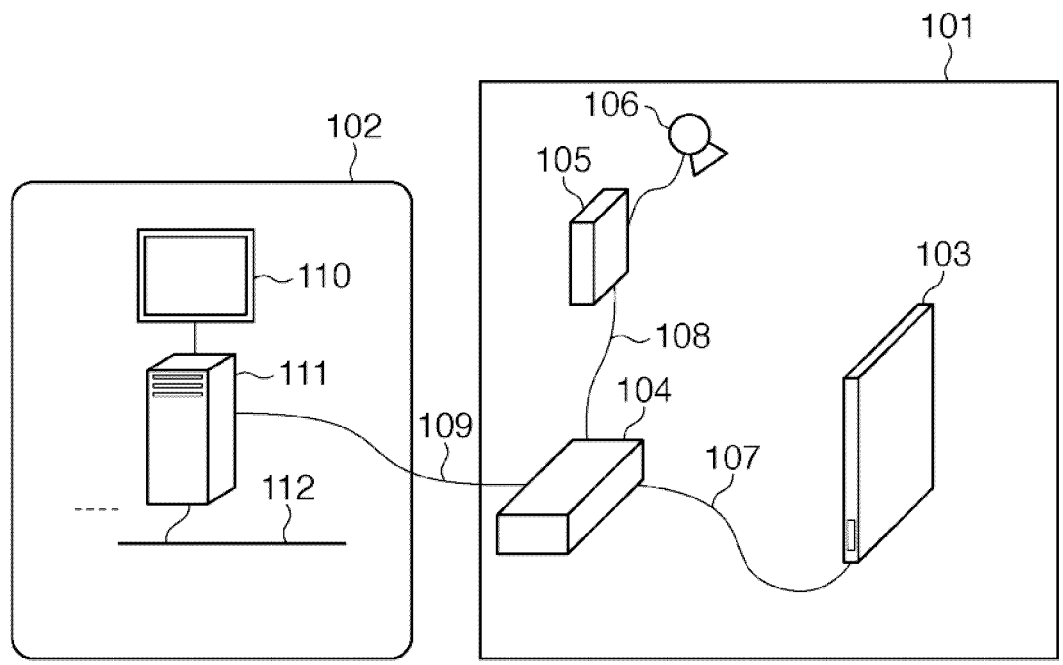
FIG. 1A is a view showing the arrangement of a radiation (X-ray) imaging system based on wired connection according to the prior art.

The arrangement of a general digital radiation system (for example, an X-ray imaging system) will be described with reference to FIG. 1A. Referring to FIG. 1A, in an X-ray room 101, X-ray imaging is performed by X-ray irradiation. A control room 102 is set near the X-ray room 101. A radiation sensor apparatus, for example, an X-ray sensor apparatus 103, generates digital X-ray image data information in response to X-rays. A plurality of X-ray sensor apparatuses 103 may exist. A synchronous repeater 104 sends the digital X-ray image data information received from the X-ray sensor apparatus 103 to an image processing apparatus 111, and controls synchronization with an X-ray generator 106. An X-ray controller 105 controls the generation of X-rays by the X-ray generator 106. The X-ray generator 106 generates X-rays under the control of the X-ray controller 105. A plurality of X-ray generators 106 may exist. If there are a plurality of X-ray generators 106, each X-ray generator 106 is associated with each entry apparatus 116 in accordance with information identifying each X-ray generator 106 and information identifying each entry apparatus 116. For example, as shown in FIG. 10A, pieces of identification information (ID1, ID2, and ID3) of the X-ray generators 106 may be associated with pieces of identification information (ID1, ID2, and ID3) of the entry apparatuses 116 in advance. Note that X-ray controller 105 may store association information of identification information. A connection cable 107 wire-connects the X-ray sensor apparatus 103 to the synchronous repeater 104. A connection cable 108 wire-connects the synchronous repeater 104 to the X-ray controller 105. A connection cable 109 wire-connects the synchronous repeater 104 to the image processing apparatus 111. A display 110 is used to display digital X-ray image data information having undergone image processing and a GUI. The image processing apparatus 111 is, for example, a PC to perform image processing. A backbone network 112 is a hospital LAN or the like for the connection of an image processing apparatus.

Figure 1B:
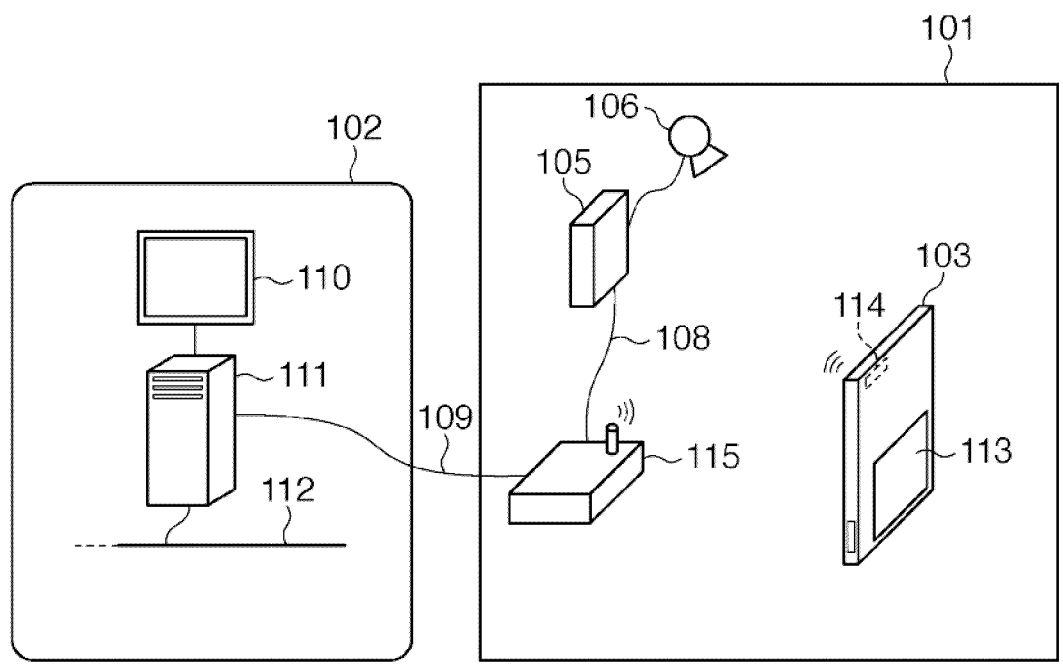
FIG. 1B is a view showing the arrangement of an X-ray imaging system based on wireless connection according to the prior art.

In general, the X-ray sensor apparatus 103 performs X-ray imaging while being fixed on a gantry or base. To perform X-ray imaging with a higher degree of freedom, an X-ray sensor apparatus may perform imaging in a free position without being mechanically fixed. In order to meet such need, there has recently appeared on the market a digital X-ray imaging apparatus of a type that wirelessly connects the X-ray sensor apparatus 103 to the synchronous repeater 104 and improves the degree of freedom of mounting the X-ray sensor apparatus 103. FIG. 1B shows the arrangement of a wireless digital X-ray imaging system.

The wireless digital X-ray imaging system will be described with reference to FIG. 1B. The basic arrangement of this system is the same as that of the digital X-ray imaging system described with reference to FIG. 1A, and the same reference numerals denote the same apparatuses. In the wireless digital X-ray imaging system, the connection cable 107 is omitted from the X-ray sensor apparatus 103, and the synchronous repeater 104 is replaced by a synchronous access point 115 additionally provided with a wireless communication function. The synchronous access point 115 faces a wireless communication unit 114 to perform wireless communication and communicates with the X-ray controller 105 and the image processing apparatus 111. In addition, the X-ray sensor apparatus 103 needs to newly incorporate a battery 113 and the wireless communication unit 114 which wirelessly communicates with the synchronous access point 115 based on IEEE802.11 standard or the like. In the arrangement shown in FIG. 1B, the X-ray sensor apparatus 103 operates on the power supplied from the battery 113, and the wireless communication unit 114 mounted in the apparatus wirelessly communicates with the synchronous access point 115, thereby sending captured X-ray image data information and exchanging control information.

Figure 2:
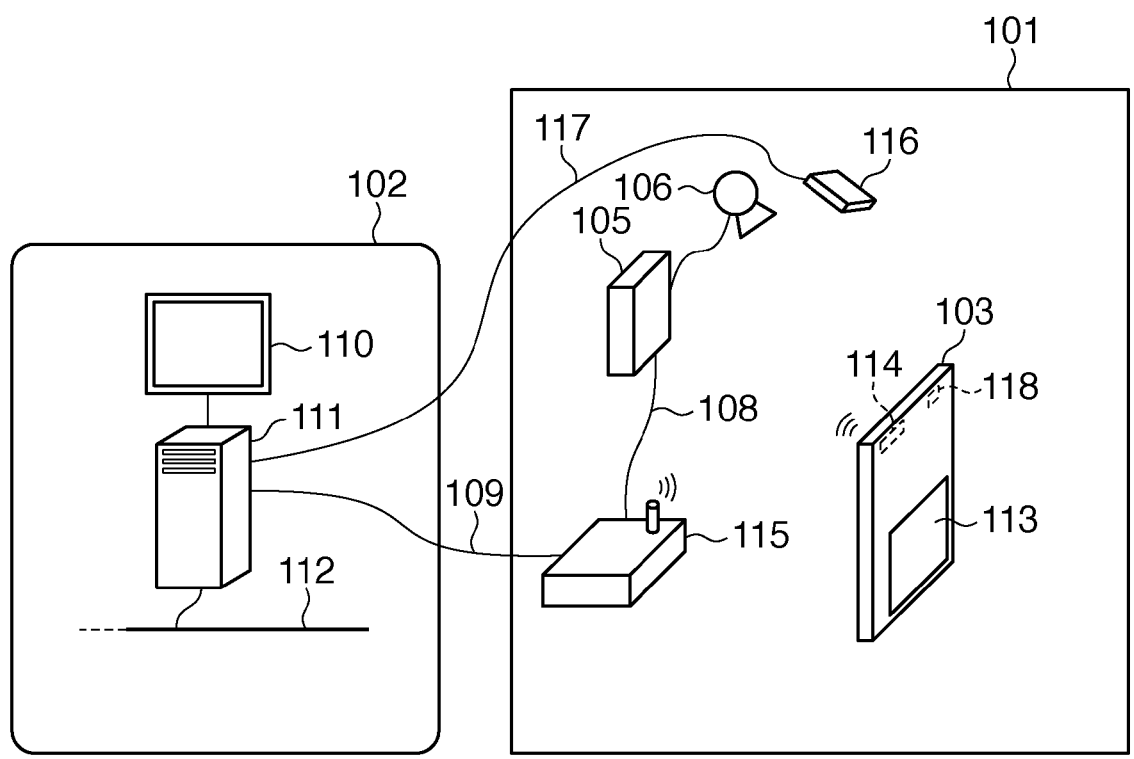
FIG. 2 is a view showing the minimum arrangement of an X-ray imaging system according to the present invention.

The arrangements of the X-ray sensor apparatus 103, entry apparatus, and access point which constitute the X-ray imaging apparatus according to this embodiment will be described with reference to FIG. 2. The entry apparatus and the access point may be discrete units or a single unit. Note that the same reference numerals as in FIG. 1 denote the same components, and a description of them will be omitted.

The entry apparatus 116 corresponds to wireless communication using IrDA or the like which allows only communication at relatively short distances. A wired connection 117 includes a USB which connects the entry apparatus 116 to the image processing apparatus 111. A close proximity wireless communication unit 118 functioning as the second wireless communication unit wirelessly communicates with the entry apparatus 116. The X-ray sensor apparatus 103 establishes a link with the entry apparatus 116 by a new wireless communication connection, and sets (configures) the wireless communication unit 114 in the X-ray sensor apparatus 103 by using communication parameters obtained via the link, thereby establishing wireless communication with the synchronous access point 115.

Figure 3:
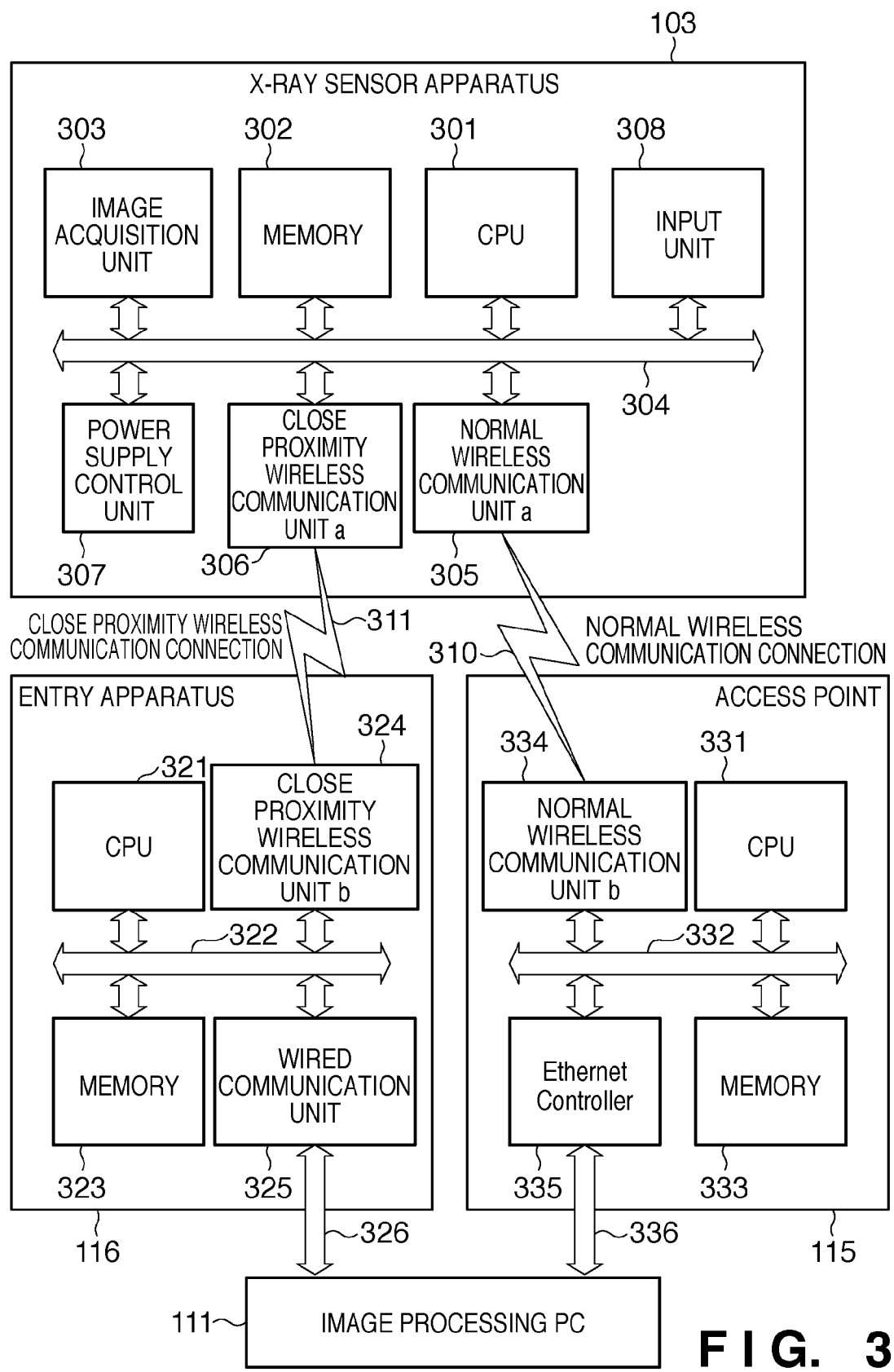
FIG. 3 is a block diagram showing the internal arrangement of each constituent element according to the present invention.

The detailed arrangement of each apparatus will be described with reference to the block diagram of FIG. 3. A CPU 301 controls the X-ray sensor apparatus 103. A memory 302 is mounted in the X-ray sensor apparatus 103 and used as a data storage area. An image acquisition unit 303 reads out image data information from a sensor unit provided for the X-ray sensor apparatus 103. A bus 304 connects the respective constituent blocks in the X-ray sensor apparatus 103. A normal wireless communication unit 305 functioning as the first wireless communication unit wirelessly communicates captured image data information and the like. A close proximity wireless communication unit 306 functioning as the second wireless communication unit performs close proximity wireless communication.

A power supply control unit 307 controls the respective power supplies of the X-ray sensor apparatus 103 in accordance with instructions from the CPU 301. An input unit 308 is provided for the X-ray sensor apparatus 103 and accepts input from the user. A normal wireless communication connection 310 is used for the communication of image data information and the like. A close proximity wireless communication connection 311 includes IrDA, TransferJet, and UWB used for sending parameters. A CPU 321 controls the entry apparatus 116. A bus 322 connects the respective constituent blocks of the entry apparatus 116.

A memory 323 is mounted in the entry apparatus 116 and used as a data storage area. A close proximity wireless communication unit 324 functioning as the second wireless communication unit wirelessly communicates with the close proximity wireless communication unit 306 by the close proximity wireless communication connection 311. A wired communication unit 325 is used to exchange data between the entry apparatus 116 and the image processing PC 111 (image processing apparatus 111). Wired communication connection 326 is a USB, FireWire, RS232C, or the like. A CPU 331 controls the access point 115. A bus 332 connects the respective constituent blocks of the synchronous access point 115. A memory 333 is mounted in the synchronous access point 115 and used as a data storage area. A normal wireless communication unit 334 functioning as the first wireless communication unit wirelessly communicates with the normal wireless communication unit 305 by the normal wireless communication connection 310. A communication controller 335 performs wired communication between the access point 115 and the image processing PC 111 (image processing apparatus 111). Wired communication connection 336 is Ethernet or the like. The image processing PC 111 performs image processing for the image data information captured by the X-ray sensor apparatus 103.

Pressing the input unit 308 of the X-ray sensor apparatus 103 will start connection processing of the X-ray sensor apparatus 103 to the access point 115. That is, upon recognizing the pressing of the input unit 308 in a form like an interrupt signal form, the CPU 301 starts a sequence for connection to the close proximity wireless communication unit 306 by the close proximity wireless communication connection 311.

Figure 4:
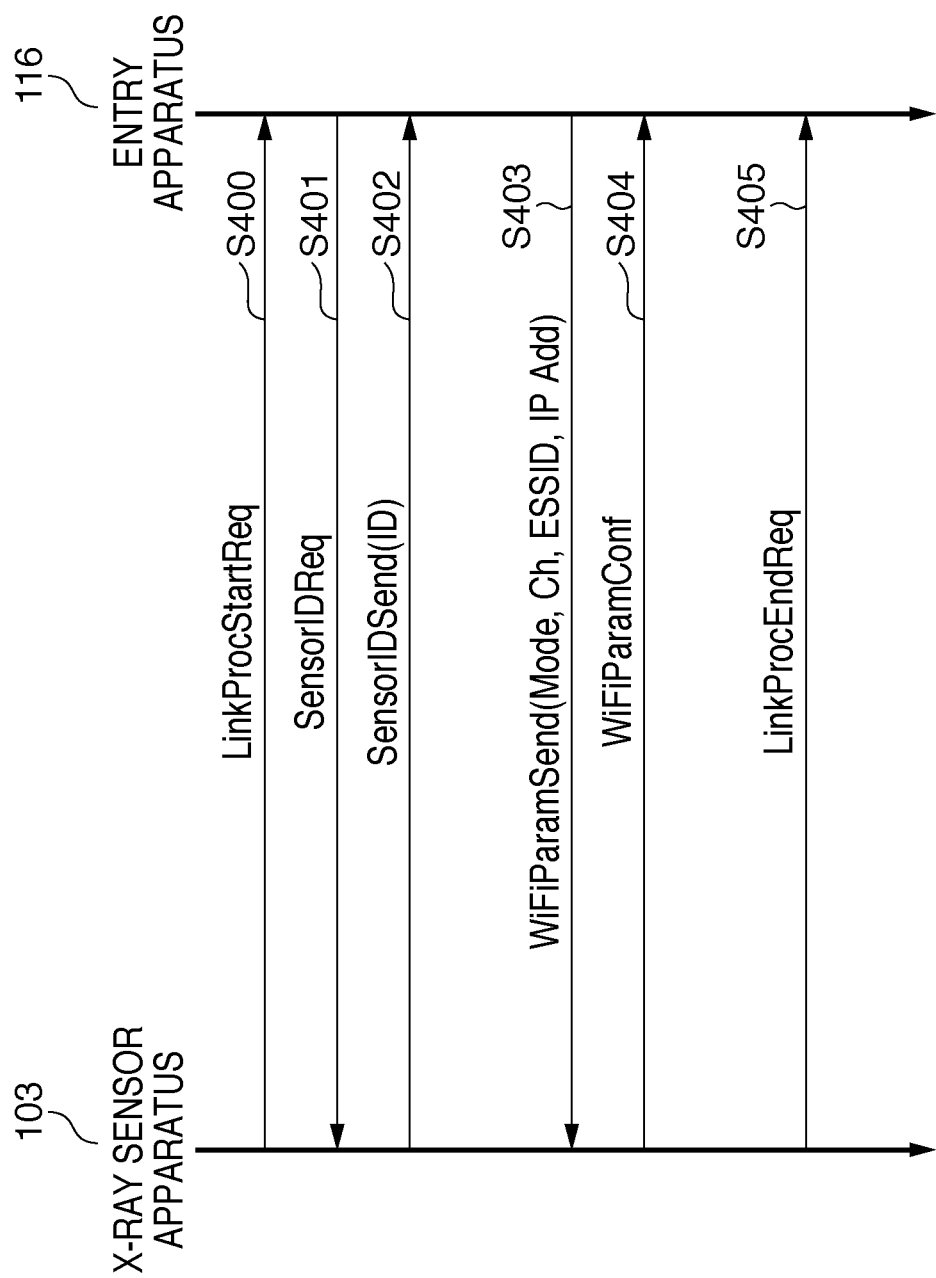
FIG. 4 is a sequence chart for Check-in processing based on close proximity wireless communication.

An example of the communication sequence exchanged by the close proximity wireless communication connection 311 will be described with reference to FIG. 4. In step S400, the X-ray sensor apparatus 103 performs connection processing for the establishment of close proximity wireless communication connection. At this time, the close proximity wireless communication unit 324 of the entry apparatus 116 is in a standby state, and hence accepts the connection processing performed by the close proximity wireless communication unit 306. In step S401, the entry apparatus 116 sends an X-ray sensor identification information request to the X-ray sensor apparatus 103 upon establishing connection. In step S402, upon receiving the identification information request, the X-ray sensor apparatus 103 returns identification information (ID information) such as a serial number unique to the X-ray sensor apparatus 103 to the entry apparatus 116.

Upon receiving the identification information (ID information), the entry apparatus 116 transfers the identification information (ID information) to the image processing PC 111 via the wired communication unit 325. Upon receiving the identification information (ID information) of the X-ray sensor apparatus 103, to which connection is to be made, via the entry apparatus 116, the image processing PC 111 searches the connection history of the X-ray sensor apparatus 103 under connection processing based on the identification information (ID information). If a match is found as a result of this processing, the image processing PC 111 prepares additional information such as correction information for the X-ray sensor apparatus 103. In addition, the image processing PC 111 accesses the access point 115 via the wired communication connection 336. The image processing PC 111 then acquires the system information (IEEE802.11a/b/g/n standards or the like) used by the access point 115 for the normal wireless communication connection 310, a physical channel, and normal wireless connection related information (parameter information), for example, an ESSID. In addition, the image processing PC 111 activates communication by the normal wireless communication unit 334 of the access point 115. The image processing PC 111 sends the normal wireless connection related information (parameter information) acquired from the access point 115 to the entry apparatus 116 via the wired communication connection 326.

Upon acquiring the normal wireless connection related information (parameter information) via the wired communication unit 325, the entry apparatus 116 sends the normal wireless connection related information (parameter information) to the X-ray sensor apparatus 103 via the close proximity wireless communication unit 324 in step S403. When receiving the normal wireless connection related information (parameter information) from the close proximity wireless communication unit 306, the X-ray sensor apparatus 103 sets connection setting values in the normal wireless communication unit 305 in accordance with the normal wireless connection related information (parameter information), and activates wireless communication by the normal wireless communication unit 305.

Upon completion of the above processing, a wireless communication link by the normal wireless communication connection 310 is established between the X-ray sensor apparatus 103 and the access point 115. Upon detecting the establishment of the link by the normal wireless communication connection 310, in step S404, the CPU 301 of the X-ray sensor apparatus 103 notifies the entry apparatus 116 via the close proximity wireless communication unit 306 that the close proximity wireless communication connection 311 has established a normal link.

When the above sequence is complete, the X-ray sensor apparatus 103 sends a disconnection request to disconnect the close proximity wireless communication connection 311 to the entry apparatus 116 in step S405. Upon receiving the disconnection request, the entry apparatus 116 terminates the communication by the close proximity wireless communication connection 311, and enters the standby state for the next connection request.

Executing the above sequence can establish wireless communication connection by the normal wireless communication connection 310 between the X-ray sensor apparatus 103 and the desired access point 115 upon pressing of the input unit 308 of the X-ray sensor apparatus 103. Note that the CPU 321 on the entry apparatus 116 or the image processing PC 111 may execute each process in the entry apparatus 116 described above. When the image processing PC 111 is to execute each process in the entry apparatus 116, the entry apparatus 116 functions as a simple bridge between the close proximity wireless communication connection 311 and the wired communication connection 326. In addition, the entry apparatus 116, the image processing PC 111, and the access point 115 may have the same arrangement.

It is also possible to further add the step of exchanging additional information to the communication sequence performed at the time of connection as described with reference to FIG. 4 or to omit an unnecessary sequence. Information to be exchanged in a single sequence may be divided to be exchanged in a plurality of sequences.

Second Embodiment

The arrangement of an X-ray imaging apparatus according to the present invention will be described with reference to the schematic diagrams of FIGS. 5, 6, and 7, assuming that the apparatus is used under an environment having a plurality of X-ray rooms. Referring to each of these diagrams, an entry apparatus 116 and an access point 115 may be discrete units or may be a single unit.

A description of part of the arrangement of an X-ray imaging room 501 in FIGS. 5, 6, and 7 which is the same as that described with reference to FIG. 2 will be omitted. A wireless communication link 119 is a wireless communication link between the synchronous access point 115 and an X-ray sensor apparatus 103. In an X-ray imaging room 502, an X-ray room 220 is an X-ray room for X-ray imaging by X-ray irradiation. A control room 221 is set near the X-ray room 220. A synchronous access point 222 can wirelessly communicate with a wireless communication unit 114 and also communicates with an X-ray controller 224 and an image processing apparatus 229. An entry apparatus 223 corresponds to wireless communication using IrDA or the like which allows only communication at relatively short distances. An X-ray controller 224 controls the generation of X-rays by an X-ray generator 225. The X-ray generator 225 generates X-rays under the control of the X-ray controller 224. A connection cable 226 is a connection cable for wired connection between the synchronous access point 222 and the X-ray controller 224. A wired connection 227 includes a USB to connect the entry apparatus 223 to the image processing apparatus 229. A connection cable 228 is a connection cable such as an Ethernet cable for wired connection between the synchronous access point 222 and an image processing apparatus 229. The image processing apparatus 229 is an image processing apparatus such as a PC which performs image processing. A display 230 is used to display digital X-ray image data information having undergone image processing and a GUI.

Figure 5:
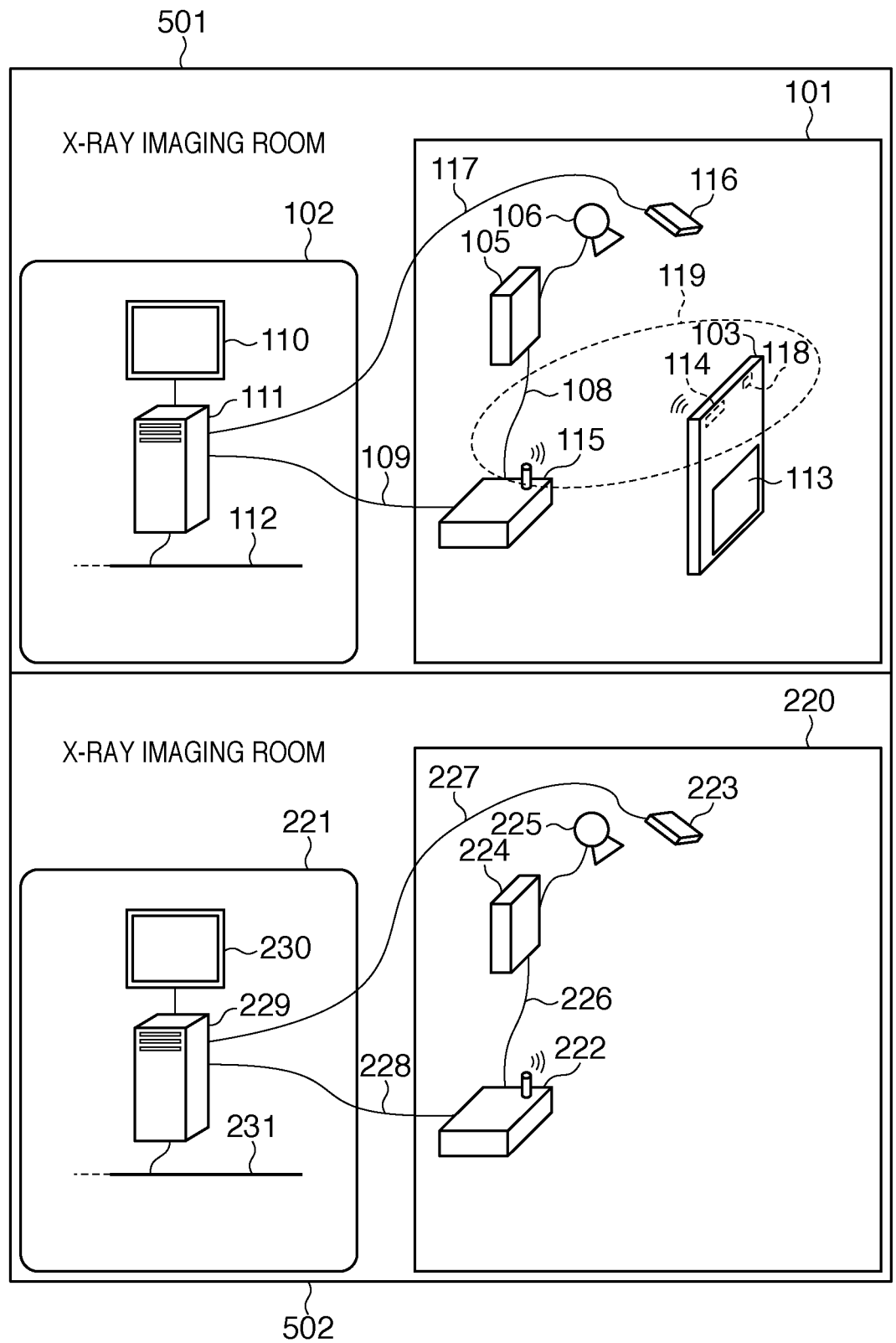
FIG. 5 is the first connection diagram under an environment including a plurality of X-ray rooms.

Assume an environment in which the X-ray imaging room 501 and the X-ray imaging room 502 are set physically near each other, and the X-ray sensor apparatus 103 is used in the X-ray imaging room 501, as shown in FIG. 5. In this environment, when using an X-ray imaging apparatus like that described in the present invention, it is necessary to prevent mutual interference between wireless communications. Different channels are set as a physical wireless channel used by the synchronous access point 115 set in an X-ray room 101 and a physical wireless channel used by the synchronous access point 222 set in the X-ray room 220. At this time, the X-ray sensor apparatus 103 has established the wireless communication link 119 with the synchronous access point 115 set in the X-ray room 101 by the procedure described in the first embodiment.

Figure 6:
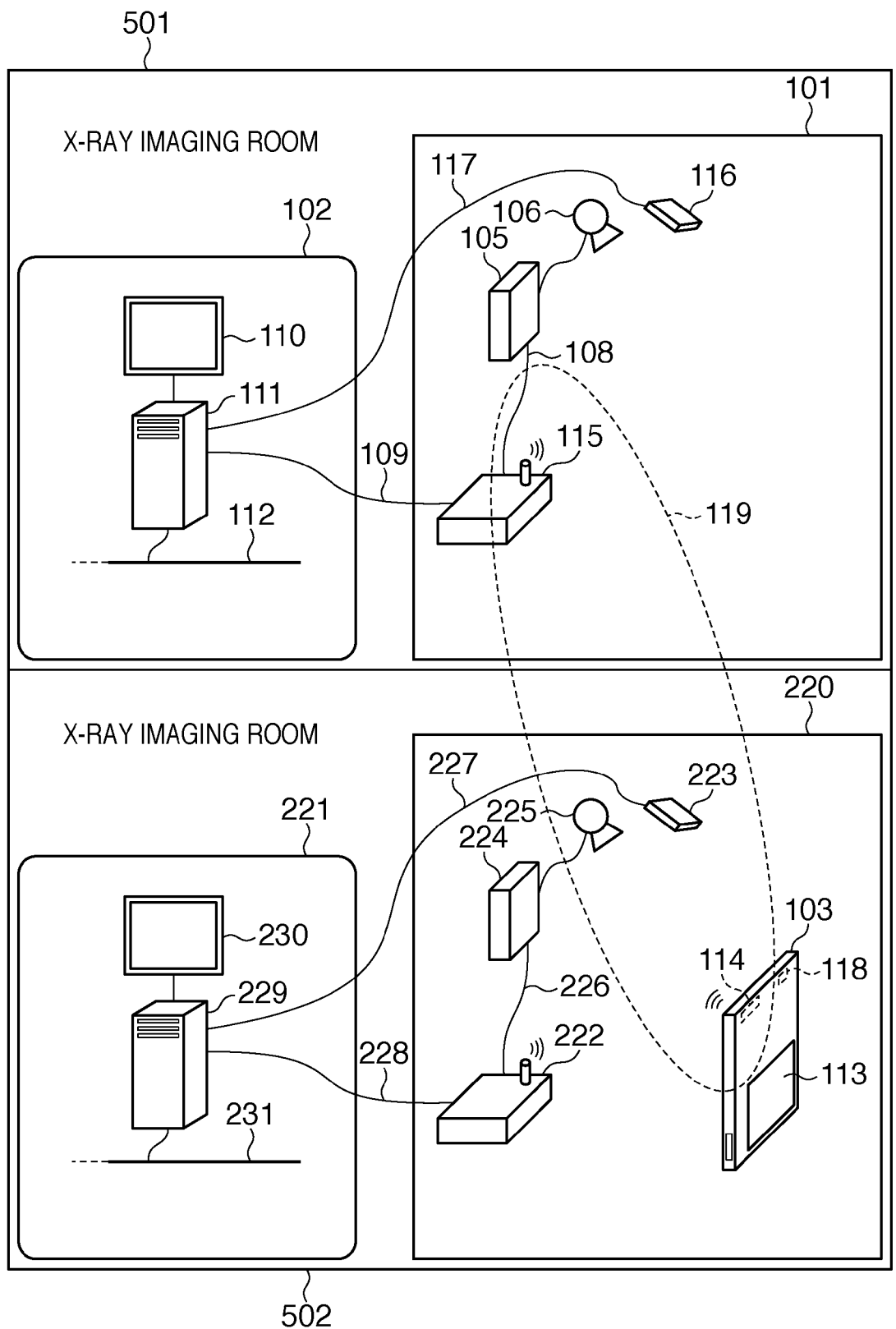
FIG. 6 is the second connection diagram under an environment including a plurality of X-ray rooms.
Figure 7:
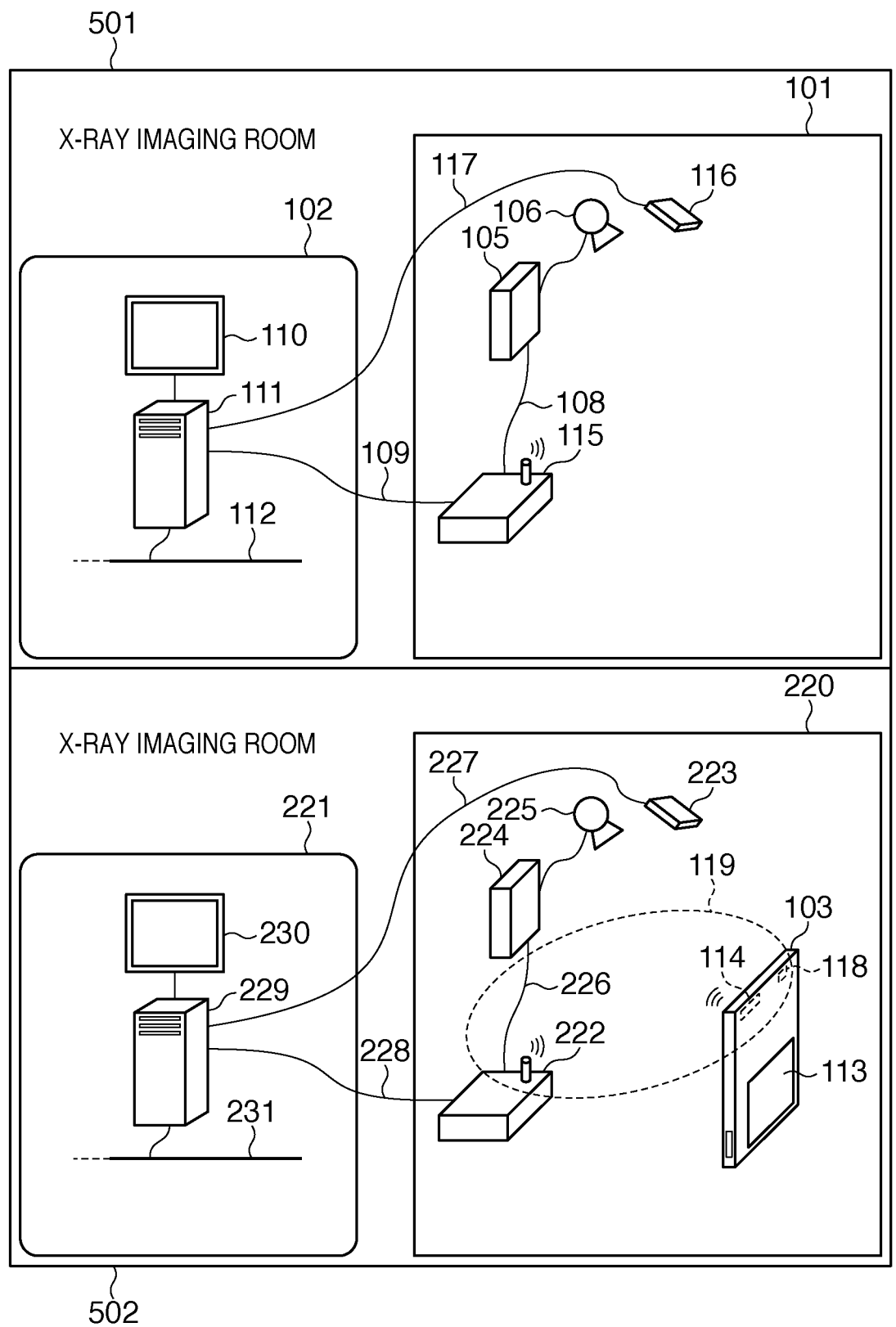
FIG. 7 is the third connection diagram under an environment including a plurality of X-ray rooms.

Assume that it is necessary to move the X-ray sensor apparatus 103 to the X-ray room 220 and perform X-ray imaging, as shown in FIG. 6. In this case, the user moves the X-ray sensor apparatus 103 to the X-ray room 220. If the user keeps the power supply of the X-ray sensor apparatus 103 ON while moving the apparatus, the wireless communication link 119 with the synchronous access point 115 set in the X-ray room 101, to which the apparatus has been connected, is kept established, as shown in FIG. 6. Even if the user temporarily turns off the power supply of the X-ray sensor apparatus 103 and moves the apparatus to the X-ray room 220, the apparatus cannot always create the wireless communication link 119 with the synchronous access point 222 set in the X-ray room 220. It is more likely that this apparatus will re-link with the synchronous access point 115 set in the X-ray room 101, to which the apparatus has been connected. Note that the block arrangements of the X-ray sensor apparatus 103, entry apparatus 116, entry apparatus 223, synchronous access point 115, synchronous access point 222, image processing apparatus 111, and image processing apparatus 229 in this embodiment are the same as those in the first embodiment described with reference to FIG. 3.

Upon bringing the X-ray sensor apparatus 103 from the X-ray imaging room 501 into the X-ray imaging room 502, the user starts connection processing from the X-ray sensor apparatus 103 to the synchronous access point 222 by pressing an input unit 308 provided for the X-ray sensor apparatus 103. The pressing of the input unit 308 is informed to a CPU 301 in the form of an interrupt signal. The CPU 301 then starts a communication sequence similar to that shown in FIG. 4 in the first embodiment. As shown in FIG. 4, in step S400, the X-ray sensor apparatus 103 performs connection processing for the establishment of close proximity wireless communication connection. At this time, a close proximity wireless communication unit 324 of the entry apparatus 223 is in the standby state, and hence accepts the connection processing performed via a close proximity wireless communication unit 306. In step S401, when connection is established, the entry apparatus 223 sends an X-ray sensor identification information request to the X-ray sensor apparatus 103. In step S402, the X-ray sensor apparatus 103 receives the identification information request, and returns the entry apparatus 223 identification information (ID information) such as a serial number unique to the X-ray sensor apparatus 103. Upon receiving the identification information (ID information), the entry apparatus 223 transfers the identification information (ID information) to the image processing PC 229 via a wired communication unit 325.

Upon receiving the identification information (ID information) of the X-ray sensor apparatus 103, to which connection is to be made, via the entry apparatus 223, the image processing PC 229 searches the connection history of the X-ray sensor apparatus 103 under connection processing based on the identification information (ID information). If a match is found as a result of this processing, the image processing PC 229 prepares additional information such as correction information for the X-ray sensor apparatus. In addition, the image processing PC 229 accesses the access point 222 via the wired communication connection 336. The image processing PC 229 then acquires the system (IEEE802.11a/b/g/n or the like) used by the access point 222 for normal wireless communication connection 310, a physical channel, and normal wireless connection related information (parameter information), for example, an ESSID. In addition, the image processing PC 229 activates communication by the normal wireless communication unit 334 of the access point 222. As described above, in order to prevent mutual interference between wireless communications, different channels are set as physical wireless channels used by the synchronous access point 115 set in the X-ray room 101 and the synchronous access point 222 set in the X-ray room 220. For this reason, the normal wireless connection related information (parameter information) used by the synchronous access point 115 differs in value from that used by the synchronous access point 222.

The image processing PC 229 sends the normal wireless connection related information (parameter information) acquired from the access point 222 to the entry apparatus 223 via the wired communication connection 326. Upon acquiring the normal wireless connection related information (parameter information) via the wired communication unit 325, the entry apparatus 223 sends the normal wireless connection related information (parameter information) to the X-ray sensor apparatus 103 via the close proximity wireless communication unit 324 in step S403. Upon receiving the normal wireless connection related information (parameter information) via the close proximity wireless communication unit 306, the X-ray sensor apparatus 103 re-sets the set value of a normal wireless communication unit 305 in accordance with the updated normal wireless connection related information (parameter information), and activates wireless communication by the normal wireless communication unit 305. In this case, the above re-setting operation may be performed only when the contents of the normal wireless connection related information (parameter information) change.

Upon completion of the above processing, the normal communication link by the normal wireless communication connection 310 between the X-ray sensor apparatus 103 and the access point 115 is disconnected. In addition, the normal communication link by the normal wireless communication connection 310 is established between the X-ray sensor apparatus 103 and the access point 222, and a state like that shown in FIG. 7 is set. The CPU 301 of the X-ray sensor apparatus 103 detects that the new link by the normal wireless communication connection 310 has been properly established. In this case, in step S404, the CPU 301 notifies the entry apparatus 223 of the proper establishment of the link by close proximity wireless communication connection 311 from the close proximity wireless communication unit 306. Upon completion of the above sequence, the X-ray sensor apparatus 103 sends a disconnection request to disconnect the close proximity wireless communication connection 311 to the entry apparatus 223 in step S405. Upon receiving this disconnection request, the entry apparatus 223 terminates the communication by the close proximity wireless communication connection 311 and enters the standby state for the next connection request.

With the execution of the above sequence, pressing an input unit 308 of the X-ray sensor apparatus 103 makes it possible to establish wireless communication connection by the normal wireless communication connection 310 between the X-ray sensor apparatus 103 and the synchronous access point 222.

Note that a CPU 321 on the entry apparatus 223 or the image processing PC 229 may execute each process in the entry apparatus 223 which has been described so far. When the image processing PC 229 is to execute each process in the entry apparatus 223, the entry apparatus 223 functions as a simple bridge between the close proximity wireless communication connection 311 and wired communication connection. It is also possible to further add the step of exchanging additional information to the communication sequence performed at the time of connection shown in FIG. 4 or to omit an unnecessary sequence. Information to be exchanged in a single sequence may be divided to be exchanged in a plurality of sequences.

Third Embodiment

A procedure to be executed when a plurality of X-ray sensor apparatuses according to the present invention are used under an environment including a single X-ray room will be described with reference to the schematic diagram of FIG. 8. An entry apparatus and an access point may be discrete units or a single unit.

Figure 8:
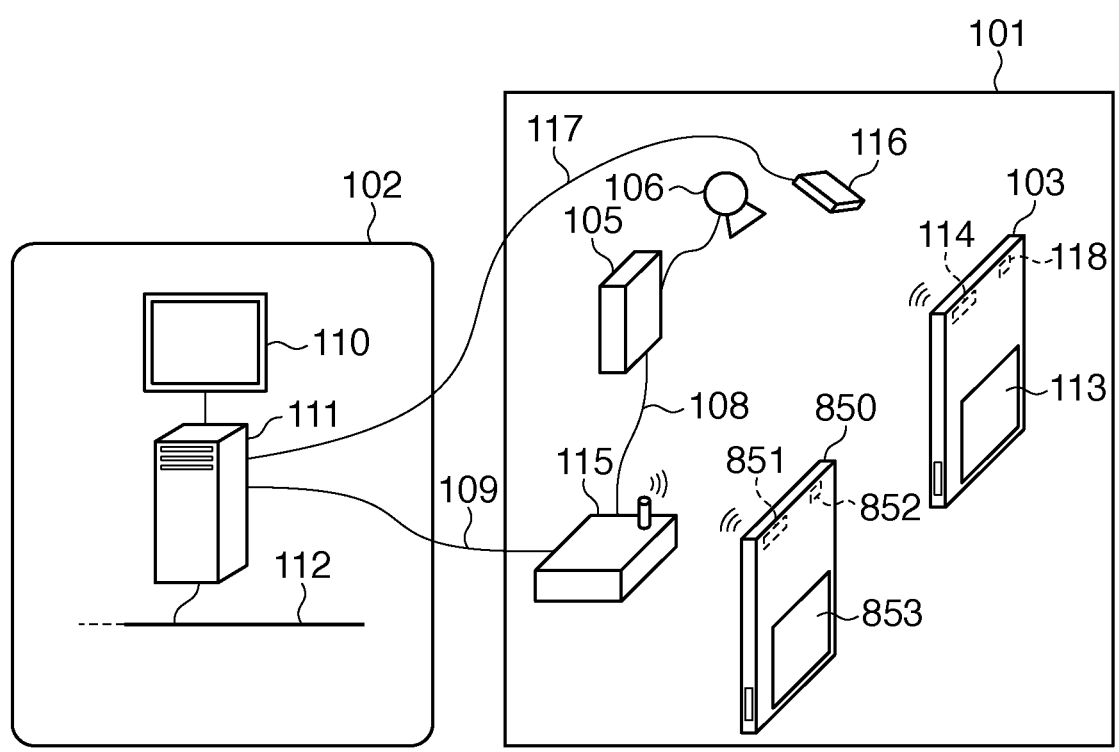
FIG. 8 is a schematic diagram in a case in which a plurality of X-ray sensor apparatuses exist in a single X-ray room.

Referring to FIG. 8, an X-ray sensor apparatus 850 generates digital X-ray image data information in response to X-rays. A wireless communication unit 851 performs wireless communication by using a synchronous access point 115, IEEE802.11 standard, and the like. A close proximity wireless communication unit 852 functioning as the second wireless communication unit wirelessly communicates with an entry apparatus 116 provided for the X-ray sensor apparatus 850. A battery 853 supplies power to the X-ray sensor apparatus 850. Note that a description of the same arrangement as that has been described above will be omitted. In this embodiment as well, the arrangements of an X-ray sensor apparatus 103, the X-ray sensor apparatus 850, the entry apparatus 116, the synchronous access point 115, and an image processing apparatus 111 are the same as those in FIG. 2 described in the first embodiment.

Assume an environment in which imaging is performed after the plurality of X-ray sensor apparatuses 103 and 850 are brought into an X-ray room 101, as shown in FIG. 8. When the X-ray imaging apparatus according to the present invention is to be used in this environment, since the connection destinations of both the X-ray sensor apparatus 103 and the X-ray sensor apparatus 850 are the synchronous access point 115, they perform wireless communication by using a single physical wireless channel. Assume that the user has performed X-ray imaging by using the X-ray sensor apparatus 103. At this time, the X-ray sensor apparatus 103 has established a wireless communication link with the synchronous access point 115 set in the X-ray room 101 by the procedure described in the first embodiment. Assume that it becomes necessary to use another X-ray sensor apparatus 850 for new imaging operation. At this time, the X-ray sensor apparatus 850 has not established a wireless communication link with the synchronous access point 115. Therefore, the user turns on the power supply of the X-ray sensor apparatus 850 and presses an input unit 308 provided on the X-ray sensor apparatus 850 to start connection processing of the X-ray sensor apparatus 850 for the synchronous access point 115. The pressing of the input unit 308 is informed to a CPU 301 in the form of an interrupt signal. The CPU 301 then starts a communication sequence shown in FIG. 4 in the first embodiment. The series of sequence processing shown in FIG. 4 is called Check-in processing.

Figure 9:
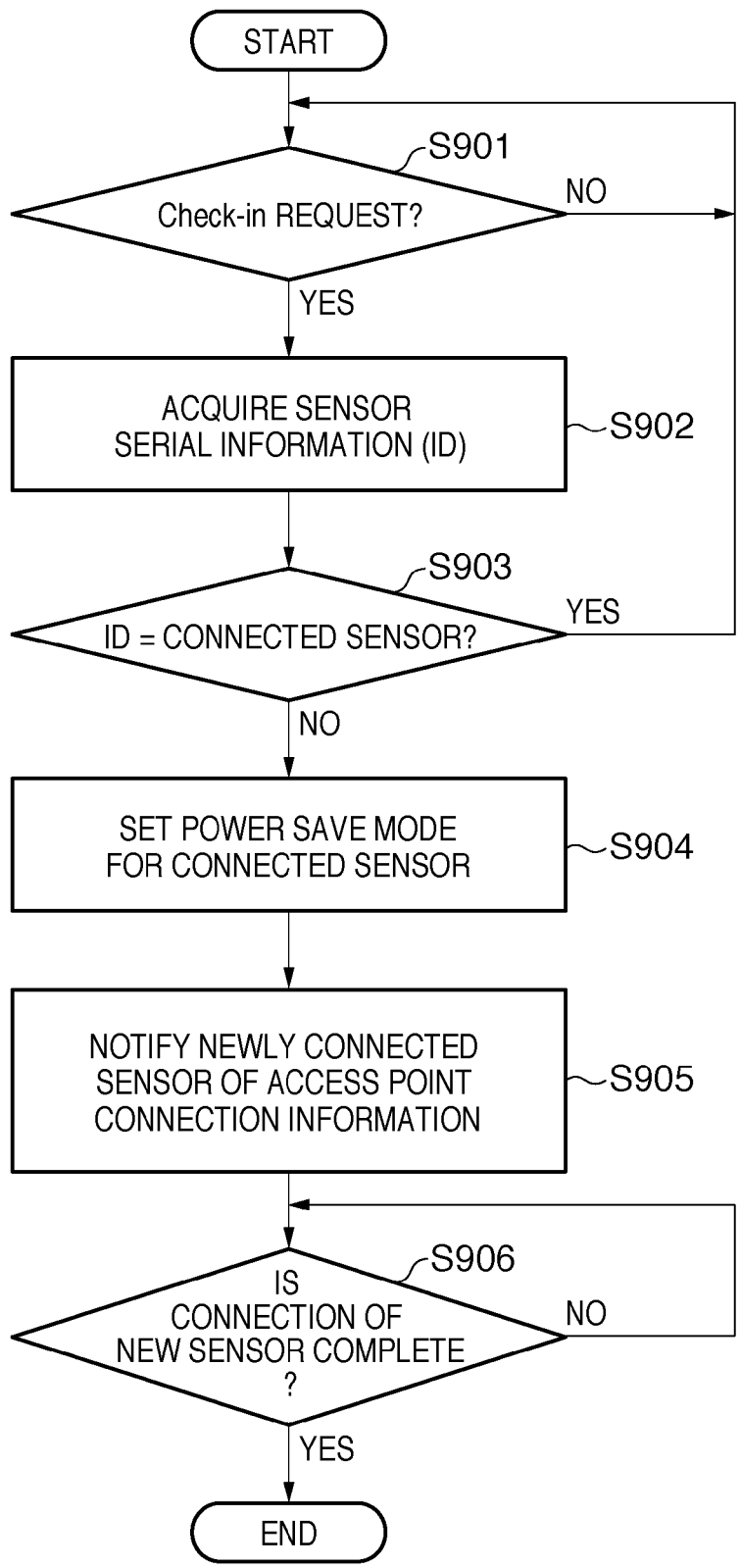
FIG. 9 is a flowchart showing operation on the system side according to the third embodiment.

The processing executed by the entry apparatus 116, the image processing PC 111, and the synchronous access point 115 in response to connection processing for the synchronous access point 115 which is started by the X-ray sensor apparatus 850 will be described with reference to the flowchart of FIG. 9.

In step S901, when the X-ray sensor apparatus 850 starts Check-in processing, the close proximity wireless communication unit 324 of the entry apparatus 116 is in the standby state, and hence accepts a connection processing request issued by a close proximity wireless communication unit 306. When connection is established (YES in step S901), the close proximity wireless communication unit 324 sends a request for the identification information of the X-ray sensor apparatus 850 to the X-ray sensor apparatus 850 in step S902. Upon receiving the identification information request, the X-ray sensor apparatus 850 returns identification information (ID information) such as the serial number unique to the X-ray sensor apparatus 850 to the entry apparatus 116. Upon receiving the identification information (ID information), the entry apparatus 116 transfers the identification information (ID information) to the image processing PC 111 via a wired communication unit 325. Upon receiving the identification information (ID information) of the X-ray sensor apparatus 850 to which connection is to be made via the entry apparatus 116, the image processing PC 111 functioning as a determination unit determines in step S903 whether the identification information is identical to that of the X-ray sensor apparatus 103 to which the image processing PC 111 is currently connected. If the identification information (ID information) is identical to that of the X-ray sensor apparatus 103 to which the image processing PC 111 has already been connected, the image processing PC 111 determines that Check-in processing has been erroneously started, and interrupts the processing. The image processing PC 111 then returns to the standby state for Check-in processing without performing anything.

If the identification information (ID information) differs from that of the X-ray sensor apparatus 103 to which the image processing PC 111 is currently connected, the image processing PC 111 controls the synchronous access point 115 via a wired communication connection 336 in step S904. The image processing PC 111 also issues an instruction (packet communication) to shift the X-ray sensor apparatus 103, which is currently connected to the synchronous access point 115 via a normal wireless communication connection 310, to the power save mode (low power consumption mode). The power save mode in this case may the intermittent beacon reception mode defined in IEEE802.11 standard or a mode of turning of the power supply of the X-ray sensor apparatus 103. In step S904, upon receiving the instruction by packet communication, the X-ray sensor apparatus 103 shifts to the pause mode, the disconnection mode, or another power save mode. That is, the X-ray sensor apparatuses other than the X-ray sensor apparatus whose normal wireless connection related information (parameter information) has been updated shift to the pause mode, the disconnection mode, or another power save mode.

Subsequently, the image processing PC 111 searches the connection history of the X-ray sensor apparatus 850 under new connection processing based on the identification information (ID information). If there is a match, the image processing PC 111 prepares additional information such as correction information for the X-ray sensor apparatus 850. The image processing PC 111 accesses the synchronous access point 115 via the wired communication connection 336. The image processing PC 111 then acquires the system (IEEE802.11a/b/g/n or the like) which the synchronous access point 115 uses for the normal wireless communication connection 310, a physical channel, and normal wireless connection related information (parameter information) such as an ESSID. The image processing PC 111 sends the normal wireless connection related information (parameter information) acquired from the synchronous access point 115 to the entry apparatus 116 via the wired communication connection 336. Upon acquiring the normal wireless connection related information (parameter information) via the wired communication unit 325, the entry apparatus 116 sends the normal wireless connection related information (parameter information) to the X-ray sensor apparatus 850 via a close proximity wireless communication unit 324 in step S905. Upon receiving the normal wireless connection related information (parameter information) via the close proximity wireless communication unit 306, the X-ray sensor apparatus 850 sets set values for a normal wireless communication unit 305 in accordance with the normal wireless connection related information (parameter information), and activates wireless communication by the normal wireless communication unit 305. Upon completion of the above processing, a wireless communication link by the normal wireless communication connection 310 is established between the X-ray sensor apparatus 850 and the access point 115. The X-ray sensor apparatus 103 shifts to the power save mode. Upon detecting that the new link by the normal wireless communication connection 310 has been properly established, the CPU 301 of the X-ray sensor apparatus 850 notifies the entry apparatus 116 of the establishment of the link from the close proximity wireless communication unit 306 in step S906 via close proximity wireless communication connection 311. Upon completion of the above sequence, the X-ray sensor apparatus 850 sends a disconnection request to disconnect the close proximity wireless communication connection 311 to the entry apparatus 116. Upon receiving the disconnection request, the entry apparatus 116 terminates the close proximity wireless communication connection 311, and enters the standby state for the next connection request.

With the execution of the above sequence, pressing an input unit 308 of the X-ray sensor apparatus 850 makes it possible to establish wireless communication connection by the normal wireless communication connection 310 between the X-ray sensor apparatus 850 and the synchronous access point 115. In addition, the X-ray sensor apparatus 103 which is not used can be shifted to the power save mode. Shifting the X-ray sensor apparatus 103 which is not used to the power save mode prolongs the service life of the battery of the X-ray sensor apparatus and effectively uses the normal wireless communication band.

If there are a plurality of X-ray sensor apparatuses and a plurality of radiation generators, it is possible to perform the processing of associating them with each other. The processing of associating them may be executed by wireless communication. For example, it is possible to execute the associating operation by communicating pieces of information identifying the respective apparatuses between the X-ray sensor apparatuses and the entry apparatuses connected to the radiation generators. For example, as shown in FIG. 10B, it is possible to associate the pieces of identification information (ID1, ID2, and ID3) of the X-ray generators with the pieces of identification information (ID1, ID2, and ID3) of the X-ray sensor apparatuses by wireless communication. The X-ray controller may store association information for the respective pieces of identification information. In this case, the respective apparatuses may be associated and combined with each other without any redundancy. Note that a CPU 321 on the entry apparatus 116 or the image processing PC 111 may execute each process in the entry apparatus 116 described so far. When the image processing PC 111 is to execute each process in the entry apparatus 116, the entry apparatus 116 functions as a simple bridge between the close proximity wireless communication connection 311 and a wired communication connection 326. It is also possible to further add the step of exchanging additional information to the communication sequence performed at the time of connection shown in FIG. 4 or to omit an unnecessary sequence. Information to be exchanged in a single sequence may be divided to be exchanged in a plurality of sequences. Although the present invention has been described by taking X-rays as a typical example of radiation, the present invention is not limited to X-rays and can implemented by other types of radiations.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2009-260451, filed Nov. 13, 2009 and 2010-241367, filed Oct. 27, 2010, which are hereby incorporated by reference herein in their entirety.

What is claimed is:

1. A radiation imaging system comprising:
a radiation imaging apparatus;
an entry apparatus which is associated with a radiation generator,
wherein said entry apparatus is configured, in response to a request received from said radiation imaging apparatus via a close proximity wireless communication connection, to send information to said radiation imaging apparatus via the close proximity wireless communication connection for connecting said radiation imaging apparatus to a wireless LAN, and
wherein the close proximity wireless communication connection has a communication range shorter than that of a wireless LAN; and
a control unit configured to control the radiation generator and said radiation imaging apparatus, which has connected to the wireless LAN based on the information which has been sent from said entry apparatus via the close proximity wireless communication connection,
wherein said control unit and said entry apparatus are connected to each other via a wired connection, and
wherein said control unit is configured to transmit the information to said radiation imaging apparatus via said entry apparatus, and said control unit is configured to receive a radiation image generated in said radiation imaging apparatus via the wireless LAN,
wherein said entry apparatus comprises an association unit configured to associate said radiation imaging apparatus with the radiation generator, and
wherein said control unit is configured to perform synchronous control of emission of radiation by the radiation generator associated by said association unit and driving of said radiation imaging apparatus.

2. The system according to claim 1, wherein said control unit is configured to perform control to synchronize driving of said radiation imaging apparatus, which has connected to the wireless LAN based on said information which has been sent from said entry apparatus via the close proximity wireless communication connection, with emission of radiation by the radiation generator which is associated with said entry apparatus.

3. The system according to claim 2, wherein said entry apparatus is configured to relay information between said radiation imaging apparatus and the wireless LAN for obtaining parameter information from the wireless LAN for establishing a wireless communication connection between said radiation imaging apparatus and the wireless LAN.

4. The system according to claim 3, wherein said entry apparatus is configured, when the parameter information of the wireless LAN has been updated, to re-establish the wireless communication connection between said radiation imaging apparatus and the wireless LAN based on the updated parameter information.

5. The system according to claim 4, wherein said control unit is configured, when a plurality of radiation imaging apparatuses are available for connection to the wireless LAN, to perform control to shift the radiation imaging apparatus which is currently connected to the wireless LAN to a power save mode, and to synchronize said radiation generator with a different one of said radiation imaging apparatuses which has requested entry to the wireless LAN via said entry apparatus.

6. The system according to claim 1, wherein said entry apparatus is configured to receive identification information for identifying said radiation imaging apparatus from said plurality of imaging apparatuses via the close proximity wireless communication connection, wherein said entry apparatus is configured to send the received identification information to the wireless LAN, and
wherein said entry apparatus is also configured to receive parameter information from the wireless LAN based on the identification information received from said radiation imaging apparatus which is used to establish the wireless communication connection by a first wireless communication unit between said radiation imaging apparatus and the wireless LAN, and
wherein said entry apparatus is also configured to send the parameter information to said radiation imaging apparatus, and
wherein said first wireless communication unit is configured to establish the wireless communication connection between said radiation imaging apparatus and the wireless LAN based on the parameter information.

7. The system according to claim 6, wherein said association unit associates said imaging apparatus with the radiation generator based on association information further communicated by the close proximity wireless communication connection.

8. The system according to claim 7, wherein said first wireless communication unit is configured, when the parameter information is updated, to re-establish the wireless communication connection between said radiation imaging apparatus and the wireless LAN based on the updated parameter information.

9. The system according to claim 8, wherein said first wireless communication unit is configured, only when the parameter information is updated and changed, to re-establish the wireless communication connection between said radiation imaging apparatus and the wireless LAN based on the updated parameter information, only when the parameter information is updated and changed.

10. The system according to claim 8, further comprising an input unit configured to establish the close proximity wireless communication connection between said entry apparatus and said radiation imaging apparatus, and
a determination unit configured, when said input unit initializes close proximity wireless communication connection processing while a previous wireless communication connection is currently established by said first wireless communication unit, to determine whether identification information of said radiation imaging apparatus, which is requesting entry to the wireless LAN through said entry apparatus by initializing the close proximity wireless communication processing, matches identification information of said radiation imaging apparatus to which wireless communication is currently established,
wherein said determination unit is configured, when said determination unit determines that the identification information matches, to terminate processing of re-establishing the wireless communication connection by said first wireless communication unit.

11. The system according to claim 10, wherein said control unit is configured, when wireless communication connection is re-established between said radiation imaging apparatus and the wireless LAN, to issue an instruction to shift said radiation imaging apparatus which is connected to the wireless LAN before re-establishment of the wireless communication connection to one of a communication pause mode, a communication disconnection mode, and a low power consumption mode, and said radiation imaging apparatus to which wireless communication connection has been established before wireless communication connection is re-established is configured to execute processing of shifting to one of a communication pause mode, a communication disconnection mode, and a low power consumption mode based on the instruction.

12. A method for a radiation imaging system comprising:

in response to a request received from a radiation imaging apparatus via a close proximity wireless communication connection, sending information from an entry apparatus associated with a radiation generator to the radiation imaging apparatus via the close proximity wireless communication connection for connecting the radiation imaging apparatus to a wireless LAN, wherein the close proximity wireless communication connection has a communication range shorter than that of a wireless LAN; and causing a control unit to controlling said the radiation generator and the imaging apparatus which has connected to the wireless LAN based on the information which has been sent from the entry apparatus via the close proximity wireless communication connection, wherein the control unit and the entry apparatus are connected to each other via a wired connection;

causing the control unit to transmit the information to the radiation imaging apparatus via the entry apparatus, and to receive a radiation image generated in the radiation imaging apparatus via the wireless LAN;

causing an association unit to associate the radiation imaging apparatus with the radiation generator; and causing the control unit to perform synchronous control of emission of radiation by the radiation generator associated with the radiation generator by the association unit and driving of the radiation imaging apparatus.

13. A non-transitory computer-readable storage medium storing a computer-executable program for causing a computer to execute the method according to claim 12.

14. A radiation imaging system comprising:

a radiation imaging apparatus;

an entry apparatus which is associated with a radiation generator, wherein said entry apparatus is configured, in response to a request received from said radiation imaging apparatus via a close proximity wireless communication connection, to send information to said radiation imaging apparatus via the close proximity wireless communication connection for connecting said radiation imaging apparatus to a wireless LAN, and wherein the close proximity wireless communication connection has a communication range shorter than that of a wireless LAN; and a control unit configured to control the radiation generator and said radiation imaging apparatus, which has connected to the wireless LAN based on the information which has been sent from said entry apparatus via the close proximity wireless communication connection, wherein said entry apparatus comprises an association unit configured to associate said radiation imaging apparatus with the radiation generator, and said control unit is configured to perform synchronous control of emission of radiation by the radiation generator associated by said association unit and driving of said radiation imaging apparatus.

* * * * *